(12) United States Patent  (10) Patent No.: US 7,612,247 B2
Oyaski  (45) Date of Patent: Nov. 3, 2009

(54) WOUND ALTERNATIVE TREATMENT SYSTEM

(76) Inventor: Michael F. Oyaski, 207 E. Highland Ave., Ebensburg, PA (US) 15931

( * ) Notice: Subject to any disclaimer, the term of this patent is extended or adjusted under 35 U.S.C. 154(b) by 304 days.

(21) Appl. No.: 11/238,348

(22) Filed: Sep. 29, 2005

(65) Prior Publication Data

US 2006/0116620 A1  Jun. 1, 2006

Related U.S. Application Data

(60) Provisional application No. 60/590,887, filed on Sep. 29, 2004.

(51) Int. Cl.
*A61F 13/00* (2006.01)
*A61M 35/00* (2006.01)
*A61M 1/00* (2006.01)
*A61L 15/16* (2006.01)

(52) U.S. Cl. .............. 602/42; 602/41; 602/43; 602/48; 602/52; 602/54; 604/289; 604/290; 604/304; 604/305; 604/313; 424/447

(58) Field of Classification Search .......... 604/289, 604/290, 304–308, 313; 602/41–43, 48, 602/52, 54; 424/447
See application file for complete search history.

(56) References Cited

U.S. PATENT DOCUMENTS 5,152,757 A * 10/1992 Eriksson ............... 604/305
5,578,022 A * 11/1996 Scherson et al. ......... 604/304
2003/0050594 A1* 3/2003 Zamierowski ........... 604/46
2003/0185704 A1* 10/2003 Bernard et al. ............ 422/37
2004/0171998 A1* 9/2004 Marasco, Jr. ............ 604/290
2005/0137521 A1* 6/2005 Stenzler .................. 604/23
2005/0261615 A1* 11/2005 Weston ................... 602/13

* cited by examiner

Primary Examiner—Michael Phillips
Assistant Examiner—Tarla R Patel
(74) Attorney, Agent, or Firm—James Ray & Assoc.

(57) ABSTRACT

A wound treatment device for treating damaged body tissue comprising an encapsulating member having a size and shape capable of being attached to a patient to encapsulate a wound. A fluid communication member is provided for introducing treatment fluid within the encapsulating means for treatment of the wound. The fluid communication member is connected with a supply means for supplying treatment fluid thereto. The fluid communication member is capable of simultaneously transmitting multiple treatment fluids from the supply means into said encapsulating member. The inner surface of the wall of the encapsulating member is textured to allow fluid flow across the wound. The encapsulating member is also formed from a clear material to permit continuous visual inspection of the wound while maintaining a sterile environment.

18 Claims, 2 Drawing Sheets

WOUND ALTERNATIVE TREATMENT SYSTEM

CROSS-REFERENCES TO RELATED APPLICATIONS

This application is based on Provisional Application Ser. No. 60/590,887, filed Sep. 29, 2004, now expired. This application is also closely related to U.S. application Ser. No. 10/790,318, entitled "Device For Treating And Promoting Healing Of Damaged Body Tissue", which is a Continuation-In-Part of U.S. application Ser. No. 09/874,539, entitled "Device For Treating And Healing Damaged Body Tissue", now abandoned. This application is also related to co-pending U.S. application Ser. No. 10/341,724, entitled "Disposable Two-Stage Pump.

FIELD OF THE INVENTION

The present invention relates, in general, to a medical device for treating damaged body tissue, and more particularly, to a device for effectively treating and promoting healing of damaged body tissue in controlled conditions.

BACKGROUND OF THE INVENTION

Approximately, 1.1 million burn patients are treated annually in the United States. There are approximately 700,000 emergency visits related to burn wounds annually. 45,000 burn patients are hospitalized annually, it is estimated that of those 4,500 die from their injuries, and another 5,000 die from infections related to the burn.

The average hospital stay for a new burn patient is from one to two weeks with an average daily medical cost of between $2,000 and $3,000. Burn injuries are second only to motor vehicle accidents as the leading cause of accidental deaths in the United States.

Burns are one of the most expensive catastrophic injuries to treat. For example, a burn of 30% of total body area can cost as much as $200,000 in initial hospitalization costs and for physicians fees. For extensive burns, there are additional significant costs, which will include costs for repeat admission for reconstruction and for rehabilitation.

Typical treatment for second and third degree burns includes the application of topical antibiotic and sterile gauze bandages to the affected area. New bandages and antibiotic are applied daily. Body fluids from the damaged skin often flow onto the bandage and dry, making bandage removal a very painful procedure for the patient. Additionally, this procedure can interrupt and significantly slow the healing process. To prevent the affected area from drying out, the bandage must be continuously moistened. Burned tissue also feels very hot and is extremely sensitive to temperature changes. Because burns covering over 75% of the body typically result in death due to the loss of bodily fluids, the patient must be continuously re-hydrated to replenish essential body fluids.

Medical personnel also treat severe wounds by suturing, applying antibiotics, and covering the wound with a gauze bandage to protect the affected area during the healing process. Similarly to burns, bodily fluids seep from the wound and adhere to the gauze bandage, causing pain to the patient during removal of the bandage. In deep wound situations, standard emergency procedure is to apply a tourniquet to the affected area to restrict the loss of blood. However, a tourniquet can damage healthy tissue by restricting the blood flow, therefore the tourniquet must be periodically loosened to prevent tissue damage and subsequent infection.

Alternative techniques are being tested and sometimes used for treatment of certain types of wounds and burns. One of these alternative techniques is hyperbaric oxygen therapy. This technique uses the same oxygen delivery system used in the treatment of diving decompression. Many of these units are large and cumbersome. Some are smaller and can be used at home, but are not portable. Another disadvantage of these units is that they only deliver vaporized or nebulized medications. Some of the clinical conditions that medical insurers have accepted hyperbaric oxygen therapy are as follows:

Enhancement of Healing in Selected Problem Wounds

Dermal Gangrene

Thermal Burns

Preparation for Skin Grafting in previously compromised tissue Necrotizing Soft Tissue Infections Radiation Necrosis: Osteoradionecrosis and Soft Tissue Radiation Necrosis Skin Graft and Skin Flap Compromise Refractory Diabetic Wounds Acute Peripheral Arterial Insufficiency Refractory Osteomyelitis There are several other methods of treating these certain types of afflictions to the body. Among those is THBO Therapy. This technique applies gases over the wound, especially oxygen and the gases are pressurized. This technique would also allow for the use of vaporized or nebulized medications. This technique is used for 90 minutes per day, 4 days a week. It has been indicated for use with diabetic skin ulcers, frostbite, burns, skin grafts, post-surgical wounds, etc. There are several disadvantages with this type of treatment. First of all, it is not intended as sole means of treatment and thus treatment medications must be applied topically at a later time. Secondly, although needed aeration of the wound occurs, there is no means for the application of moisture to the wound during treatment. Consequently, treatment is followed with external moist media treatment and redressing, which can expose the wound to contaminants. Another disadvantage of this method is that because the treatment is not continuous and the wound requires redressing, monitoring of the wound is performed in a manner similar to gauze treatment.

Another technique being used is that of an encapsulator. This technique is designed for fluid immersion of wound. Growth factors, new skin cells and medication can be applied to the wound. Monitoring of the wound healing is done via fluid output (Chemistry microbiology.) Results of animal studies show significant reduction in wound healing as a result of the "wet" (vinyl encapsulation chamber with saline) therapy. A major disadvantage of this method is that aeration of the wound is not available. The system would have to be removed to provide for aeration, which can result in contamination. Another disadvantage of this method is pressurized treatment on the wound cannot be performed.

In addition to hospitals and burn units, there is a need in the art for a miniature and convenient topical wound care product that delivers hyperbaric oxygen topically to open wounds which can be used in the field by emergency medical technicians and by military personnel. This device can be used to provide immediate on-site treatment to wounds and/or battlefield injuries.

There is a further need in the art for an alternative wound treatment device which is inexpensive and portable, can ease patient discomfort, allow for continuous monitoring of the wound, provide for proper aeration of the wound, allow for the application of several types of treatment media to the wound while maintaining a sterile environment.

SUMMARY OF THE INVENTION

The invention is directed to a wound treatment device for treating damaged body tissue. The wound treatment device comprises an encapsulating means having a size and shape capable of encapsulating a wound. The encapsulating means includes a wall having an inner and an outer surface. The inner surface of the wall is capable of being positioned adjacent the wound. Means are provided for attaching the encapsulating means to one of a patient and a surface to encapsulate the wound and a fluid communication means is provided for introducing treatment fluid within the encapsulating means for treatment of the wound. The fluid communication means is connected with a supply means for supplying treatment fluid thereto. The inner surface of the wall of the encapsulating means is textured to allow fluid flow across the wound. The encapsulating means is also formed from a clear material to permit continuous visual inspection of the wound. The fluid communication means is capable of simultaneously transmitting multiple treatment fluids from the supply means into said encapsulating means.

OBJECTS OF THE INVENTION

It is therefore the primary object of the present invention to provide a wound alternative treatment device that provides ports for both liquid and gas to permit changing the media type without changing the dressing.

It is yet another object of the invention to provide a wound treatment system with an encapsulating means having a textured inner surface, which promotes fluid flow.

It is still yet another object of the invention to provide a wound treatment device having a disposable pump to control fluid input.

It is another object of the invention to provide a wound treatment device, which is inexpensive to produce, and portable to allow for on-site field treatment and home-based treatment of wounds.

It is yet another object of the invention to provide a wound treatment device which allows for the attachment of a monitoring device to record the patient's response to the treatment.

It is still a further object of the invention to provide a wound treatment device, which is capable of transferring one, or more mediums simultaneously, maintaining a sterile environment for the wound, permit visual inspection of wound, and prevent dehydration.

It is yet another object of the invention to provide a wound treatment device which allows for a controlled wound healing environment in terms of temperature, pressure and chemical i.e. oxygenation, medications, growth factors, new skin cells and the like.

In addition to the above-described objects and advantages of the wound alternative treatment device, various other objects and advantages of the present invention will become more readily apparent to the persons who are skilled in the same and related arts from the following more detailed description of the invention, particularly, when such description is taken in conjunction with the attached drawing figures and the appended claims.

DETAILED DESCRIPTION OF THE INVENTION

Figure 1:
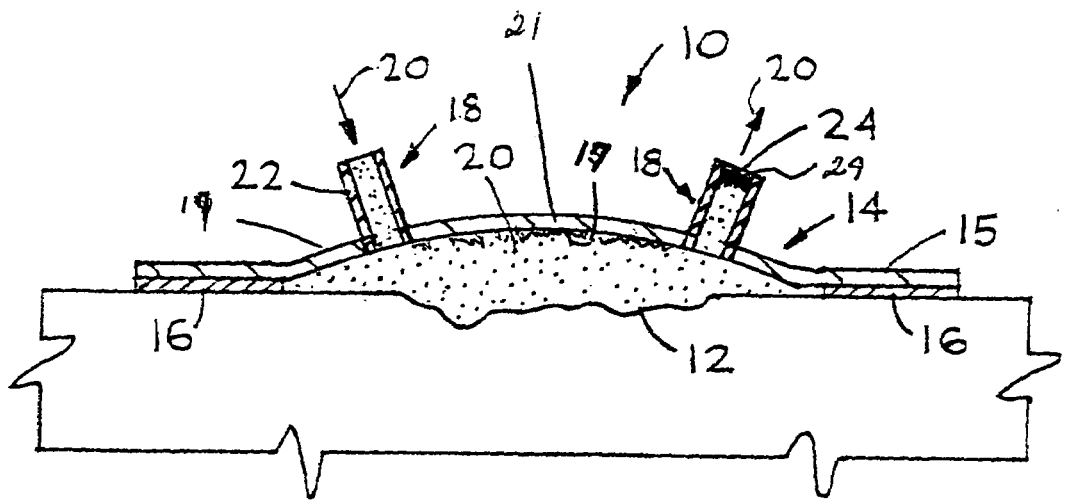
FIG. 1 is a side lavational section view of the wound treatment device according to the invention.

Prior to proceeding to a more detailed description of the invention, it should be noted that identical components having identical functions have been designated with identical reference numerals for the sake of clarity.

Now referring to FIG. 1, illustrated therein is a device, generally designated 10, for treating and promoting healing of damaged body tissue 12. The device 10 comprises an encapsulating means 14 disposed on the body tissue 12 for controlling the environmental condition surrounding the tissue. The encapsulating means 14 has a size and shape capable of encapsulating the wound 12. The encapsulating means 14 comprises a wall 21 having an inner 17 and an outer 19 surface. The inner surface 17 is capable of being positioned adjacent the wound 12. The encapsulating means 14 creates a sterile environment and further allows for the temperature and humidity to be controlled for the patient's comfort, and to enhance the healing process. Preferably, the encapsulating means 14 comprises a flexible bladder, which is formed from a transparent plastic material to enable continuous visual inspection of the wound during treatment. The inner surface 17 of the flexible bladder is textured to allow for fluid flow across the wound regardless of a patient's position. Thus, the patient's comfort is greatly increased because he/she has greater freedom of movement.

A means 16 is provided for attaching the encapsulating means 14 to either the patient or another surface. This means is preferably an adhesive or a double-sided tape. Alternatively, a mechanical attaching means, such as Velcro™ or snaps, or a combination of adhesive and mechanical attaching means may be provided for attaching the encapsulating means to another surface and/or the patient or for wrapping the encapsulating means 14 about a patient's appendage and attaching the encapsulating means 14 to itself. The attaching means 16 is disposed on the perimeter of at least one side of the encapsulating means 14. The attaching means 16 will secure the encapsulating means 14 around the damaged tissue or wound 12, sealing the affected area from exterior environmental conditions.

The device also comprises a fluid communication means, generally designated 18, for introducing treatment fluid within the encapsulating means 14 to allow at least one of a predetermined treatment fluid 20 to communicate and/or contact the damaged tissue/wound 12 without having to remove the encapsulating means 14. Preferably, the fluid communication means 18 comprises at least one inlet port 22 extending through the wall 21 of the encapsulating means 14 and tubing 23 (see FIG. 3) connected with the at least one inlet port 22 for transporting the treatment fluid 20 for a supply means 27 (see FIG. 3) through the inlet port 22 and into the encapsulating means 14. The fluid communication means 18 may also comprise multiple inlet ports 50 having tubing 23 attached thereto (see FIG. 3) for simultaneously transmitting multiple treatment fluids from the supply means 27 into the encapsulating means 14.

The inlet port tubing 23 may be in contact with at least one of a heating and cooling unit, preferably within the supply means 27, for controlling the temperature of the treatment fluid 20 entering the encapsulating means 14.

The supply means 27 for supplying the treatment fluid 20 to the wound treatment device may be a disposable two-stage pump which is the subject of U.S. Pat. No. 7,331,770 The supply means 27 is capable of supplying a treatment fluid 20 in the form of gas, a liquid, or simultaneously both a gas and a liquid. The supply means 27 is further capable of supplying fluid treatment 20 which includes medication, growth factors, new skin cells, and the like. A control means may also be provided, preferably within the supply means 27, for controlling the pressure within the encapsulating means 14. A monitoring device can also be provided for monitoring and recording a patient's reaction to treatment of the wound 12.

The fluid communication means 18 may also include at least one outlet port 24 extending through the wall 21 of the encapsulating means 14. This outlet port 24 also includes tubing 25 (see FIG. 3) connected with the at least one outlet port for at least one of removing treatment fluids 20 from the encapsulating means 14 and for applying a vacuum thereto. Either the tubing 25 connected to the outlet port 24 or the outlet port 24 itself can include at least one filter 29 for filtering the treatment fluids 20 exiting the encapsulating means 14. Alternatively, the filtering means may be provided within the supply means 27. A means, not shown, may be provided in the supply means 27 for re-introducing the filtered treatment fluid into the fluid communication means 18 to increase the lifespan of the treatment fluid 20.

It is noted that the device preferably includes a separate outlet port 24 removing the treatment fluids 20 from within the encapsulating means, however inlet port 22, as discussed above, may also be utilized as an outlet port for the treatment material by reversing the flow of the treatment fluid 20 and/or applying a vacuum to this port 22 when cessation of treatment is desired.

Also, note that it is desired that the wound treatment device, including the supply means, is formed from lightweight, inexpensive material so that it may be readily used in the field and may be disposed of to avoid contamination to other patients which may occur as a result of repeated use.

Figure 2:
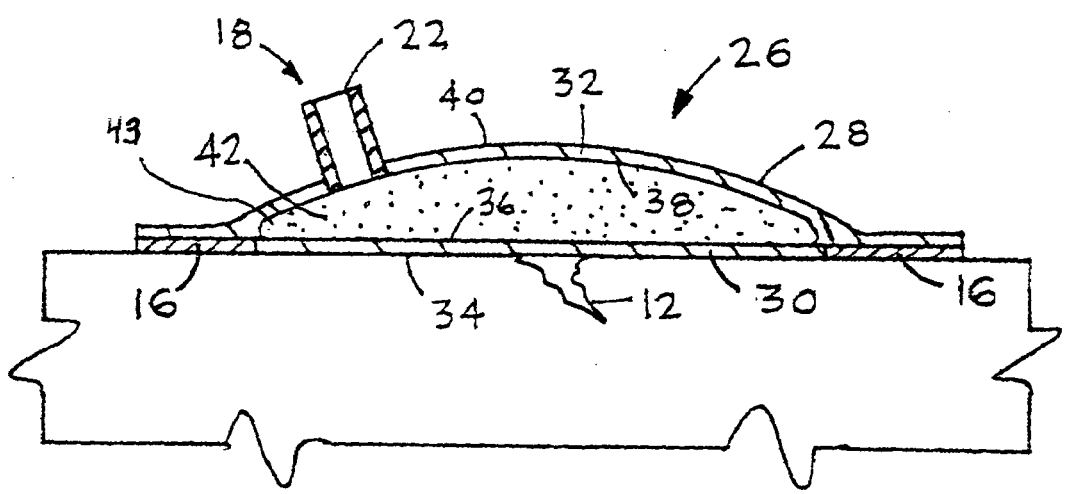
FIG. 2 is a side lavational section view of the wound treatment device according to an alternative embodiment of the invention.

Now referring more particularly to FIG. 2 of the drawings. Illustrated therein is a device, generally designated 26 for treating and healing damaged body tissue 12. The device 26 comprises an encapsulating means 28 having a first flexible bladder 30 and a second flexible bladder 32. The second bladder 32 has a predetermined greater elasticity than the first bladder 30 for enabling the device 26 to act as a tourniquet. The first bladder 30 has a first surface 34 and a second surface 36 and the second bladder 32 has a third surface 38 and a fourth surface 40. The first surface 34 of the first bladder 30 is disposed on the wound 12. Preferably, the material of the encapsulating means 28 is transparent so that the wound is visible therethrough. It is also preferred that an adhesive 16 is disposed on the perimeter of at least one of the first surface 34 of the first bladder 30 and the third surface 38 of the second bladder 32, for securing the encapsulating means 28 to the area surrounding the damage tissue 12. Preferably, a pressurized fluid 42 is disposed into a pocket 43, formed intermediate the second surface 36 of the first bladder 30 and the third surface 38 of the second bladder 32 for controlling the environmental conditions surround the damage tissue/wound 12 and for applying controlled pressure to the wound 12. It is preferred that the pressurized fluid 42 is at lest one of a gas and a liquid. A transfer means, generally designated 18, is disposed on the encapsulating means 28 to allow the pressurized fluid 42 to communication with the encapsulating means 28, whereby controlled pressure can be applied to the wound to seal the area around the wound and to promote healing. Preferably the transfer means 18 is at least one inlet port 22.

Figure 3:
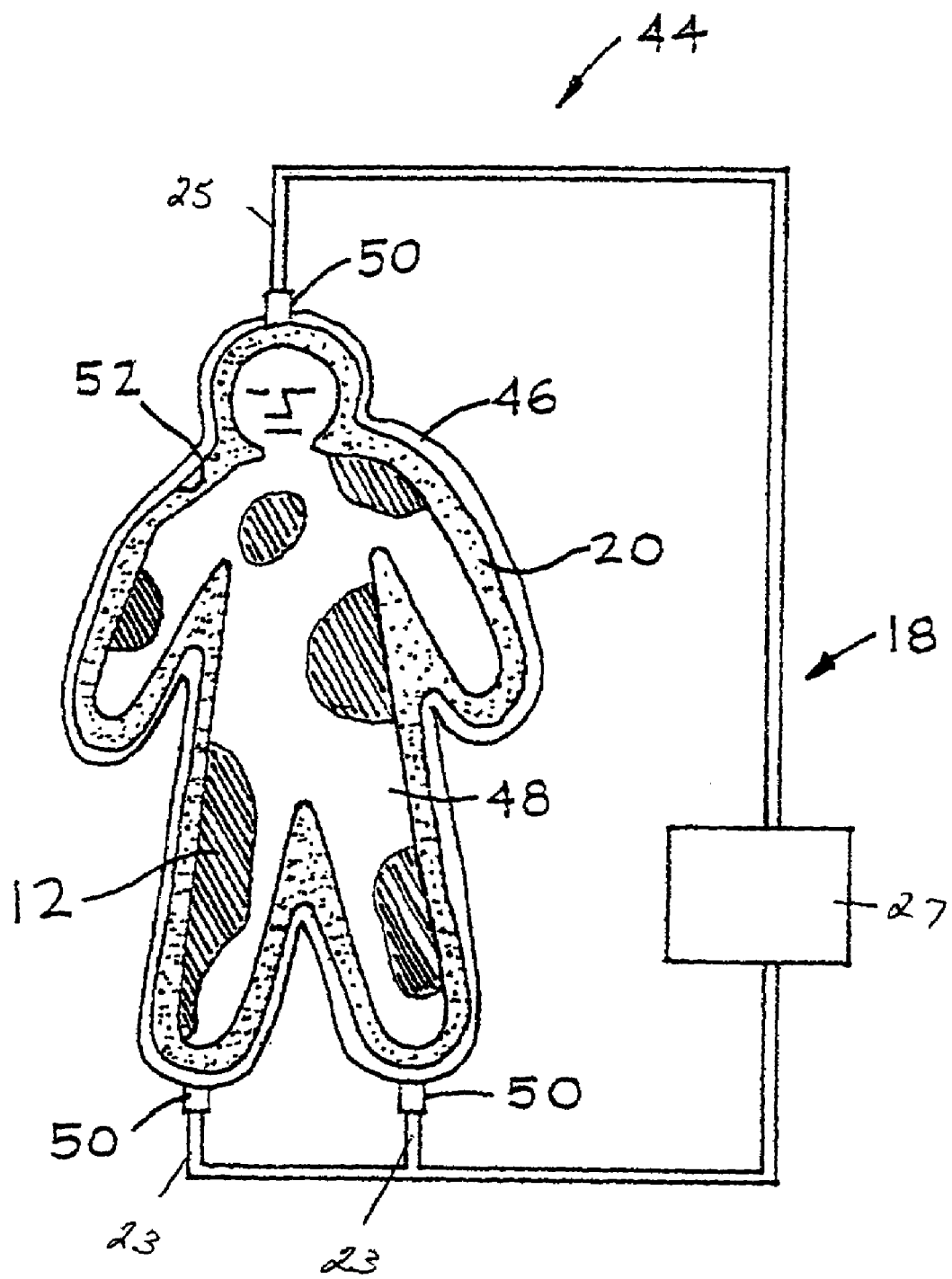
FIG. 3 is a top view of the wound treatment device according to another embodiment of the invention.

Now referring more particularly to FIG. 3 of the drawings. Illustrated therein is a device, generally designated 44, for treating and promoting healing of damaged body tissue 12. The device 44 comprises a bodysuit 46 of a predetermined size, shape, and material for enclosing at least a portion of a body 48 when larger and/or multiple areas of tissue are damaged. Preferably, the material of the bodysuit 46 is transparent to allow the body to be viewed through the bodysuit. Also, preferably the inner surface 52 of the bodysuit 46 is textured to permit fluid circulation around the body are that directly contacts the bodysuit 46, especially when the patient is lying down. A fluid communication means, generally designated 18, is disposed on the bodysuit 46 to allow at least one of a predetermined treatment material 20 to communication with the bodysuit 46 without removing the bodysuit 46, whereby the tissue 12 can be effectively treated and healed in controlled environmental conditions. Preferably, the fluid communication means 18 is at least one port 50 of a predetermined size and shape, and a circulation or supply pump 27, as discussed in detail above. It is preferred that the fluid communication means 18 includes a plurality of ports 50 to control the temperature, humidity, and to circulated liquids, medications and pain killers around the body 48. It will also be obvious to the reader that a bodysuit 46 that envelops the entire body will have additional ports for feeding, breathing and for the elimination of bodily waste.

Operation damaged body tissue 12, such as a burn or wound, on a portion of the body 48 is covered with the encapsulating means 14. The encapsulating means 14 is sealed at its perimeter around the damaged body tissue 12. Antibiotics, growth factors, gases and liquids, and the like are injected into the inlet port 22. Inserting a suitable pharmaceutical fluid through the inlet port 22 and extracting the fluid through the outlet port cleanses the affected area. Treatment material is then reapplied to the clean tissue 12 through the inlet port 22. The encapsulating means 14 remains in place throughout the healing process, maintaining a sterile, aerated, humidity and temperature-controlled environment. When deeper penetration is required, medications and pain relievers can be applied under pressure to the specific area.

In the FIG. 2 embodiment, the encapsulating means 28 exerts pressure on a wound, similar to a tourniquet, but in a controlled manner. The pressure in the encapsulating means 28 can be regulated to apply the necessary force required to decrease blood loss.

In the FIG. 3 embodiment, the bodysuit 46 encapsulates a larger area of damaged body tissue. Temperature and humidity can be controlled in the bodysuit 46, while medications and pain relievers can be circulated around the entire area to treat the damaged body tissue 12 and promote healing. In specific circumstances, the encapsulated are can be submerged in water to relieve the pressure on the damaged tissue. The affected area remains sterile and dry. When a full bodysuit 46 is required, the bodysuit 46 can be designed to provide breathing and feeding apparatus and elimination of bodily wastes.

Although the invention has been shown in connection with certain specific embodiments, it will be readily apparent to those skilled in the art that various changes in form and arrangement of parts and method may be made to suit requirements without departing from the spirit and scope of the invention.

I claim:

1. A wound treatment device for treating damaged body tissue, said wound treatment device comprising:
   (a) an encapsulating means having a size and shape capable of encapsulating a wound, said encapsulating means includes a wall having an inner and an outer surface, said inner surface capable of being positioned adjacent such wound;
   (b) means for attaching said encapsulating means to one of a patient and a surface to encapsulate such wound;
   (c) a first fluid communication means for introducing a liquid treatment fluid within said encapsulating means;
   (d) a two stage pump supply means for supplying said treatment fluid to said first fluid communication means for treatment of such wound, wherein said treatment fluid supplied is liquid, gaseous or separately and simultaneously both liquid and gaseous; and
   (e) a second fluid communication means for introducing a gaseous treatment fluid within said encapsulating means.

2. A wound treatment device as claimed in claim 1 wherein said encapsulating means includes a flexible bladder.

3. A wound treatment device as claimed in claim 2 wherein said inner surface of said flexible bladder encapsulating means is textured to allow fluid flow across such wound.

4. A wound treatment device as claimed in claim 1 wherein said encapsulating means is formed from a clear material to enable visual inspection of such wound.

5. A wound treatment device as claimed in claim 1 wherein said means for attaching said encapsulating means to one of a patient and a surface includes one of an adhesive and a double-sided tape.

6. A wound treatment device as claimed in claim 1 wherein said mean for attaching said encapsulating means to one of a patient and a surface includes a mechanical attaching means.

7. A wound treatment device as claimed in claim 1 wherein said fluid communication means includes at least one inlet port extending through said wall of said encapsulating means and tubing connected with said at least one inlet port for transporting said treatment fluid through said at least one inlet port and into said encapsulating means.

8. A wound treatment device as claimed in claim 1 wherein said fluid communication means includes a first outlet port extending through said wall of said encapsulating means and tubing connected with said first outlet port for at least one of removing said liquid treatment fluid and applying a vacuum to said encapsulating means and a second outlet port extending through said wall of said encapsulating means and tubing connected with said second outlet port for at least one of removing said gaseous treatment fluid and applying a vacuum to said encapsulating means.

9. A wound treatment device as claimed in claim 8 wherein said tubing connected with said at least one outlet port includes at least one filter for filtering said treatment fluids exiting said encapsulating means and said device further includes means for re-introducing said filtered treatment fluid into said encapsulating means to increase the lifespan of said treatment fluid.

10. A wound treatment device as claimed in claim 1 wherein said fluid communication means is in contact with at least one of a heating and cooling unit, for controlling a temperature of each said treatment fluid entering said encapsulating means.

11. A wound treatment device as claimed in claim 1 wherein each of said communication means is capable of at least one of removing said treatment fluid and applying vacuum to such wound.

12. A wound treatment device as claimed in claim 1 wherein said device further includes a means for monitoring and recording a patient's reaction to treatment of such wound.

13. A wound treatment device as claimed in claim 1 wherein said fluid supply means is capable of supplying at least one of medication, growth factors and new skin cells to said first fluid communication means.

14. A wound treatment device as claimed in claim 1 wherein said fluid communication means includes multiple input ports extending through said wall of said encapsulating means wall and tubing connected with said multiple input ports for simultaneously transmitting multiple treatment fluids from said supply means into said encapsulating means.

15. A wound treatment device as claimed in claim 1 further including control means for controlling a pressure within said encapsulating means.

16. A wound treatment device as claimed in claim 1 wherein said encapsulating means includes a body suit for encapsulating a patient's body.

17. A wound treatment device as claimed in claim 1 wherein said encapsulating means includes a first and second flexible bladder, said first bladder being positioned adjacent a wound and said second bladder being positioned a predetermined distance from said first bladder to form a pocket therein, said pocket capable of receiving a fluid from said fluid communication means enabling said wound treatment device to act as a tourniquet.

18. A wound treatment device as claimed in claim 1 wherein said device is disposable.

* * * * *